United States Patent [19]

Neumann

[11] 4,399,487
[45] Aug. 16, 1983

[54] INSULATED PLUG-IN MODULE

[75] Inventor: Leopold Neumann, Lexington, Mass.

[73] Assignee: Siemens AG, Berlin and Munich, Fed. Rep. of Germany

[21] Appl. No.: 393,684

[22] Filed: Jun. 30, 1982

Related U.S. Application Data

[63] Continuation of Ser. No. 186,534, Sep. 12, 1980, abandoned.

[51] Int. Cl.³ .............................................. H05K 7/06
[52] U.S. Cl. .................................... 361/391; 361/394; 361/395; 361/399; 361/424
[58] Field of Search ............ 339/17 M, 17 LM, 17 N; 174/35 R, 52 R; 361/391, 393, 395, 394, 399, 415, 422, 424

[56] References Cited

U.S. PATENT DOCUMENTS 3,052,821 9/1962 Scoville .............................. 361/399
3,475,657 10/1969 Knowles ............................. 361/395
3,668,476 6/1972 Wrabel ................................ 361/395

FOREIGN PATENT DOCUMENTS 2752783 4/1979 Fed. Rep. of Germany .
948023 1/1964 United Kingdom ................ 361/394

OTHER PUBLICATIONS

Brochure "Models 78341A/78342A Monitors–Patient Monitoring", 1978, Hewlett-Packard, Medical Products Group, Waltham, MA.

Primary Examiner—G. P. Tolin
Attorney, Agent, or Firm—Karl F. Milde

[57] ABSTRACT

A cabinet is disclosed having recesses receiving sliding insulated plug-in modules, the modules having front connectors for receiving input signals and rear coupling portions, each module having printed circuit boards and a shield therefor.

7 Claims, 6 Drawing Figures

INSULATED PLUG-IN MODULE

This application is a continuation, of application Ser. No. 186,534, filed 9/12/80, now abandoned.

BACKGROUND OF THE INVENTION

1. Field of the Invention

This invention relates to an insulated plug-in module of high voltage resistivity for insertion into a cabinet, housing, box or the like. In particular, this invention relates to a plug-in module comprising an outer case of highly insulating plastic into which a packet is inserted which contains printed circuit boards retained between a front and a rear wall, the printed circuit boards carrying structural elements needed for energy and/or signal transmission. More particularly, this invention relates to a plug-in module for a medical instrument, preferably for a patient monitoring device.

2. Description of the Prior Art

Slide-in units or modules having an outer case and printed circuit boards can be used for diverse measuring devices in a great variety of measurement sectors. However, a preferred field of application is that of electromedicine. Here a great variety of physiological signals are taken from the body of a patient and displayed e.g. on the screen of a cathode ray tube or on the paper of a recorder or on similar display devices. The signals picked up involve such diverse signals as e.g. electrocardiogram (ECG) signals, blood pressure signals, respiration signals, $CO_2$ signals (carbon dioxide in the blood or respiration gas), temperature signals, etc. During measurement, the patient has to be protected by all means from any unwanted electric exposure.

SUMMARY OF THE INVENTION

1. Objects

It is an object of this invention to provide an electric slide-in unit or functional plug-in module which is well insulated and which has high voltage resistivity.

It is another object of this invention to provide a plug-in module which is versatile and which can be used for a large variety of applications.

It is still another object of this invention to provide a plug-in module which, a minimum of separate parts, can be used with large versatility.

It is still another object of this invention to provide a plug-in module which can be used in a medical instrument, particularly in a bedside unit of a patient monitoring device.

It is still another object of this invention to provide a plug-in module which has its components and parts inserted in a case, the components and parts being arranged such that they are visible when the module is taken out of its case.

2. Summary

According to this invention, a plug-in module for insertion into a recess of a cabinet is provided which contains a plurality of structural elements and components for signal processing. The components are connected with each other as to form internal electrical circuits. The plug-in module also contains a front wall for carrying connection devices such as connectors. These connection devices receive input signals which are specific to a certain application, for instance electromedical signals. The plug-in module further contains a rear wall for carrying rear coupling devices.

A larger printed circuit board extends from the front wall to the rear wall. This board supports a group of the mentioned structural elements and of the components. This group of components forms circuits on this larger board which are specific to the intended application of the module. A smaller printed circuit board is mounted on the back wall and extends toward the front wall. This smaller board is arranged parallel to the larger board. Thus, it leaves free some space in the region of the front wall which may be used for mounting an additional board. The mentioned smaller board supports a number of the structural elements and of the components. These components form internal electrical circuits which are identical for various applications.

The smaller and the larger board are inserted, together with the rear wall, in a case. The front wall to which the larger circuit board is connected forms the front face of the case. The case may be provided with sliding or guiding means to facilitate insertion into the opening of the cabinet. The case preferably may be made of a highly insulating plastic.

The plug-in module according to the invention has a design which is very versatile in use, since circuits which are application-specific are separated from circuits which are not. Only comparatively few parts are needed.

The foregoing and other objects and advantages of the invention will be apparent from the following more particular description of preferred embodiments of the invention, as illustrated in the accompanying drawings.

DETAILED DESCRIPTION OF THE PREFERRED EMBODIMENTS

Figure 1:
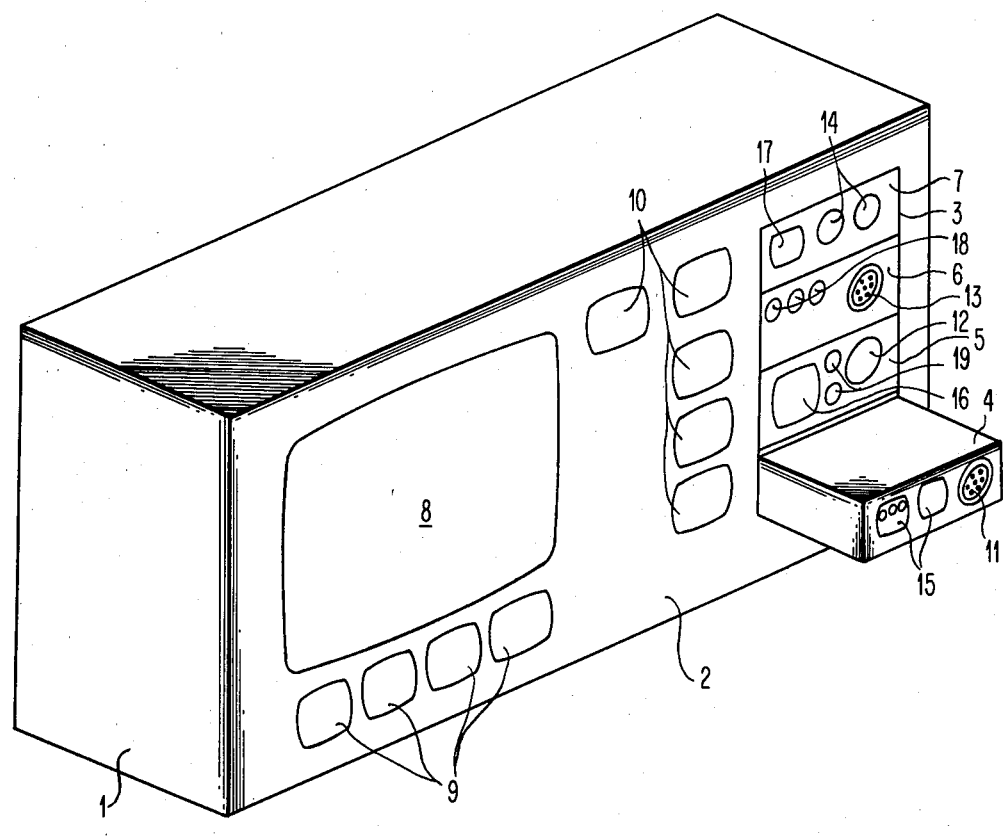
FIG. 1 is a perspective view of a medical instrument having a recess for housing plug-in modules according to the invention.

FIG. 1 shows the basic mechanical construction of an electromedical monitoring device with four plug-in modules. Such a patient monitoring device may preferably be used as a bedside device. The monitoring device comprises a rectangular housing or cabinet 1 having a front wall or front panel 2. On the right side of the front wall 2, an opening or recess 3 leads into the interior of the cabinet 1. The opening 3 is rectangular. Into this opening 3 there can be inserted four plug-in modules 4, 5, 6, and 7, all designed according to this invention. They can be inserted horizontally one above the other. Sliding means (not shown) provide a safe guidance and a sliding contact with the side walls of the recess 3.

The monitoring device is also equipped with a cathode ray tube 8, which serves to display the different signals entering the device from the different plug-in modules 4-7. Various elements 9, 10 on the front panel 2 of the monitoring device are control and indicating elements, such as key switches, LED indicating fields, etc. Their arrangement on the monitoring device is purely schematic in FIG. 1. In a practical design, therefore, any other arrangement may be chosen.

As has been indicated, the monitoring device of FIG. 1 is an electromedical device. The plug-in modules 4 to 7 form part of the transmission system for physiological signals. These signals are picked up on a patient's body by means of suitable electrodes, detectors, or sensors. For this purpose, sensors (not shown) are positioned on the patients's body and coupled via a signal cable (not shown) to the respective plug-in module 4 to 7. To this end, the plug-in modules 4 to 7 contain jacks or connectors 11 to 14 for corresponding plugs of the signal cables. The remaining elements 15 to 19 in FIG. 1 are, in purely schematic illustration, data keys or LED indicator fields of the plug-in modules 4 to 7. In FIG. 1, for example, the plug-in module 4 on the bottom may be a $CO_2$ plug-in module, the two central plug-in modules 5 and 6 may be plug-in modules for blood pressure and temperature measurements, respectively, and the plug-in module 7 on the top may serve for ECG measurements.

Figure 2:
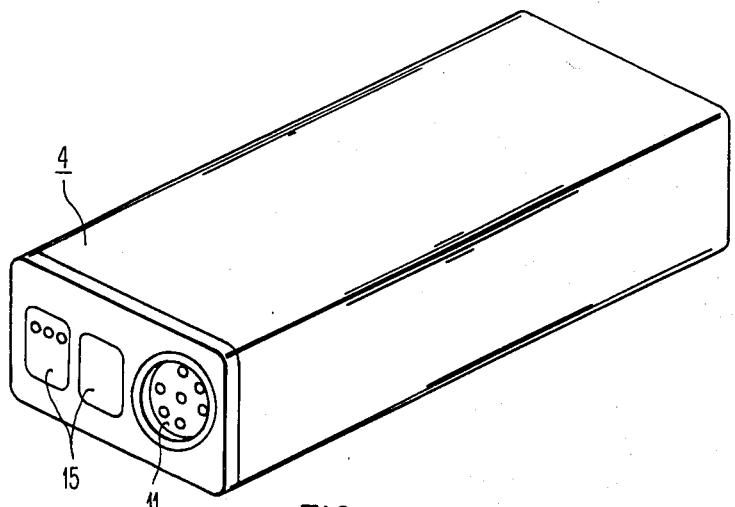
FIG. 2 is a perspective view of a plug-in module.
Figure 3:
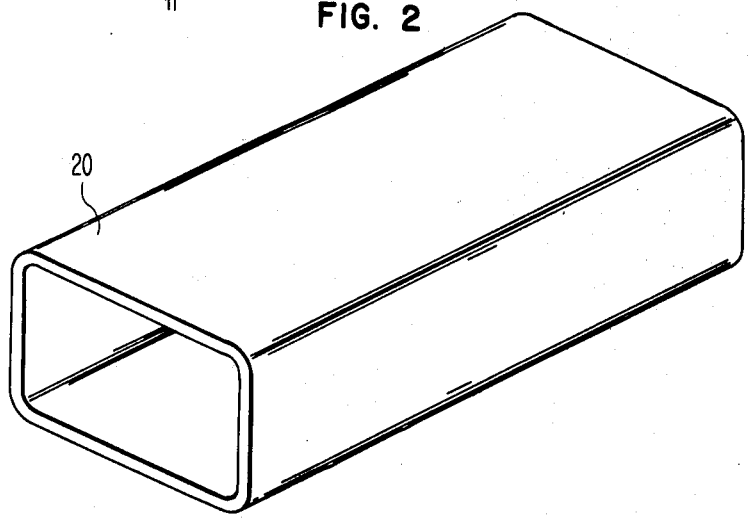
FIG. 3 is a perspective view of the highly insulating case of a plug-in module.

In FIG. 2 is shown an embodiment of a plug-in module according to the invention, for example, of the plug-in module 4 in FIG. 1. The module 4 is an elongated body of rectangular shape. As shown in FIG. 3, each module 4 to 7 comprises a shell or case 20 which is open on the front. The case 20 is made of highly insulating plastic, e.g., amino-butadienestyrene (ABS).

Figure 4:
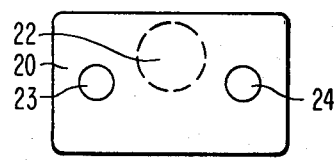
FIG. 4 is a planar view of the back wall of the case shown in FIG. 3.

In FIG. 4 is illustrated the back wall 21 of the case 20. In the disk-like center portion 22 (indicated by broken lines) this back wall 21 is thinner than in the surrounding wall portions. The thin wall portion ensures an especially close coupling of a primary transducer for energy transmission (not shown in FIGS. 1–4) arranged on the side of the device, to a secondary transducer (not shown in FIGS. 1–4) arranged inside the respective plug-in module in direct contact with the back wall 21 of the case 20. The transducer on the side of the monitoring device and the transducer on the side of the module are thus fitted together as a galvanically separating coupling point for energy transmission from the monitoring device to the plug-in module. Energy transmission may take place as soon as the plug-in module has been brought to its end position in the recess 3 of the monitoring device.

What has been said about the energy coupling applies in principle also to the signal transmission between the plug-in module and the monitoring device in both directions. Here, too, a galvanically separating coupling is provided. For the purpose of signal transmission from the plug-in module to the monitoring device a light signal emitter, in particular a luminescence diode, is provided on the module side. Associated to the light emitter is a light receiver, in particular a photoresistor, on the device side. Correspondingly, for signal transmission in the reverse direction, a light emitter on the device side is positioned oppositely to a light receiver on the module side. In order that light can pass unhindered between the module and the monitoring device, two plastic windows 23 and 24 for light transmission in both directions are disposed in the back wall 21 of the case 20 of each plug-in module 4 to 7.

Figure 5:
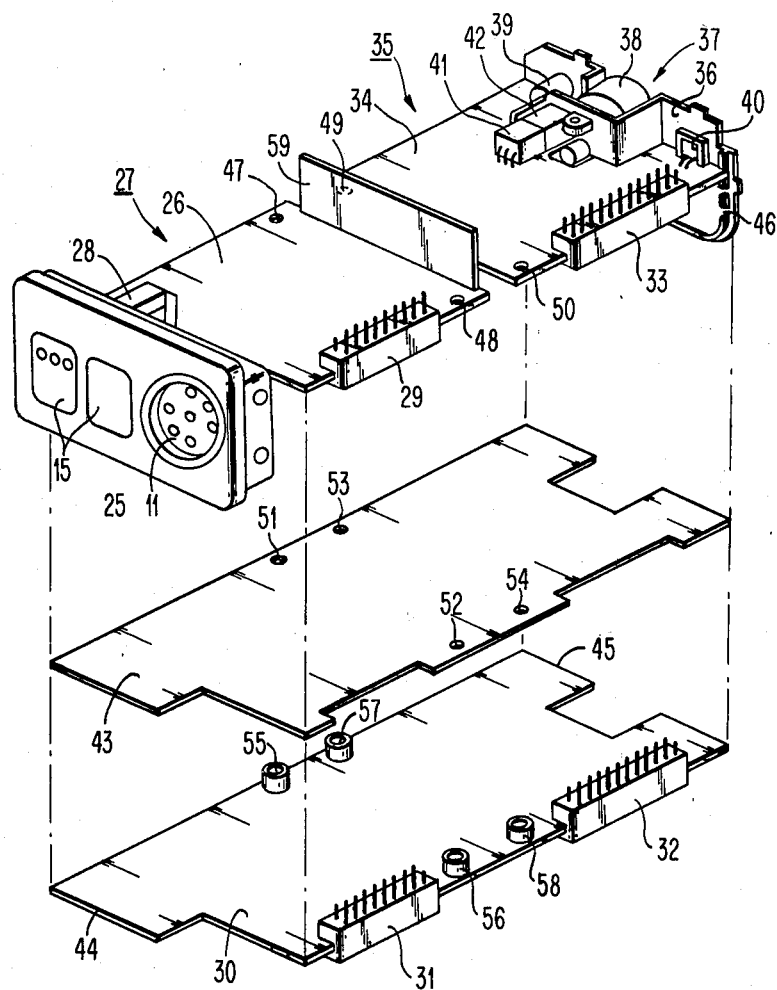
FIG. 5 is an explosive view of a plug-in module showing the correlation of individual printed circuit boards and parts thereof to a front wall and to a back wall.

In FIG. 5 is shown in an exploded view the correlation of individual printed circuit boards of regular size or parts thereof to the front wall and back wall, the assembly forming a laminate packet. As will be noted, a layered concept is used. The electrically shielding front wall, which is also the end face of a plug-in module, is denoted as 25 in FIG. 5. In the present case, the front wall 25 may be again e.g. the end face of an ECG slide-in unit. A first half-part 26 of a regular-size printed circuit board is mounted, e.g. screwed, horizontally on the back of the front wall 25. The front wall 25 and first board half-part 26 together form a first mounting unit 27. For different applications of the plug-in module, that is for different types of input signals, this mounting unit 27 is formed signal-specifically. Thus, the first board half-part or sub-board 26 carries only those electrical or electromechanical components of the internal circuit which are different from application to application and depend on the selected kind of input signal, for example, ECG, blood pressure signal, temperature signal, $CO_2$ signal, respiration signal, etc. Typical signal-specific components of the first sub-board 26, which are not specifically shown in the drawing, are e.g. different preamplifiers, frequency filters, etc.

The circuit thus formed can be electrically connected via a cable cord 28 to the contacts of the signal input jack or connector 11 and the data input or indicating keys 15, on the one hand. On the other hand, the circuit can be connected by means of a laterally arranged first plug or connector 29 to those electric circuits which are arranged e.g. on an additional printed circuit board 30 of the laminate packet. The additional board 30 therefore has a first counter-plug or connector 31 matching the first connector 29 of the first board-half 26. The additional board 30 is of regular size. It is arranged horizontally and below the first board-half 26. The pins of connector 29 are not shown in FIG. 6.

A third electrical connection path leads via a second plug or connector 32 on the additional (not divided) board 30, and via a matching counter-plug 33 on the lateral edge of a rear or second board-half 34 to a second mounting unit, namely the rear mounting part 35 of the laminate packet. The board-halves 26 and 34 are aligned with respect to each other.

In the second mounting part 35, the second board-half 34 is permanently assigned to the yoke-shaped back wall 36. That is, the second board-half 34 is e.g. tightly screwed to this back wall 36. The back wall 36 is made, for example, of metallized plastic. The second mounting part 35 is identical for all plug-in modules. It carries at least some of those components of the internal electrical or electromechanical circuit which are identical for all plug-in modules regardless of the respective signal-specific use of the module. In the present case, the second mounting part 35 supports preferably all structural elements needed for energy transmission and for signal exchange between the plug-in modules and the monitoring device. Accordingly, the yoke-shaped back wall 36 carries in its yoke recess 37 a secondary transducer 38 for energy transmission from the monitoring device to the module. Also, two inserts 39 and 40 are provided on the left and right side of the yoke recess 37. In the insert 39 is inserted a light emitter, e.g. a luminescence diode, for signal transmission from the plug-in module to the monitoring device. The insert 40 contains a light receiver, e.g. a photoresistor, for signal transmission from the monitoring device toward the plug-in module.

The electronic elements needed for energy and signal transmission, as in particular an analog-digital converter for the signal conversion, are disposed (not shown) on the second board-half 34. For establishing an electric contact between structural elements disposed on the second board-half 34 and structural elements seated on the back wall 36, two matching contact plugs 41 and 42 are used. The first plug 41 is fastened on the second board-half 34, and the second plug 42 is connected to the back wall 36.

The rear mounting part 35 thus formed, which is identical for all plug-in modules 4-7, can now be assembled with a front-side mounting part 27 of any desired design. Thus, many variations of modules are obtained.

This assembling is effected as follows:

First, with interposition of a flexible shielding foil 43 (e.g. aluminum), the front-side mounting part 27 is attached to the front edge 44 and the back-side mounting part 35 to the rear edge 45 of the undivided printed circuit board 30. These two edges 44, 45 of the board 30 engage in niches 46 of the front wall 25 of the first mounting part 27 and of the back wall 36 of the second mounting part 35. In FIG. 5, only the niches of the back wall 36 is visible, but the front wall 25 has a corresponding niche.

The mounting parts thus attached are then additionally secured by screws through extending screw holes 47, 48, and 49, 50 of the half-boards 26 and 34, respectively, through corresponding holes 51 to 54 in the interposed shielding foil 43, to threaded protrusions or ferrules 55 to 58 of the continuous printed circuit board 30. Said ferrules can be mounted between intermediate foil 43 and both outer boards 30 and 26 or 34. Thus, the mounting packet shown in the center of FIG. 6 will result. In this packet, the circuits of the first mounting unit 27 and those of the second mounting unit 35 are further shielded from each other at the joint by an additional vertical shielding sheet 59. This sheet 59 may consist e.g. of copper or aluminum. As shown in FIG. 5, this vertical shielding sheet 59 is mounted on the rear edge of the first board-half 26.

Figure 6:
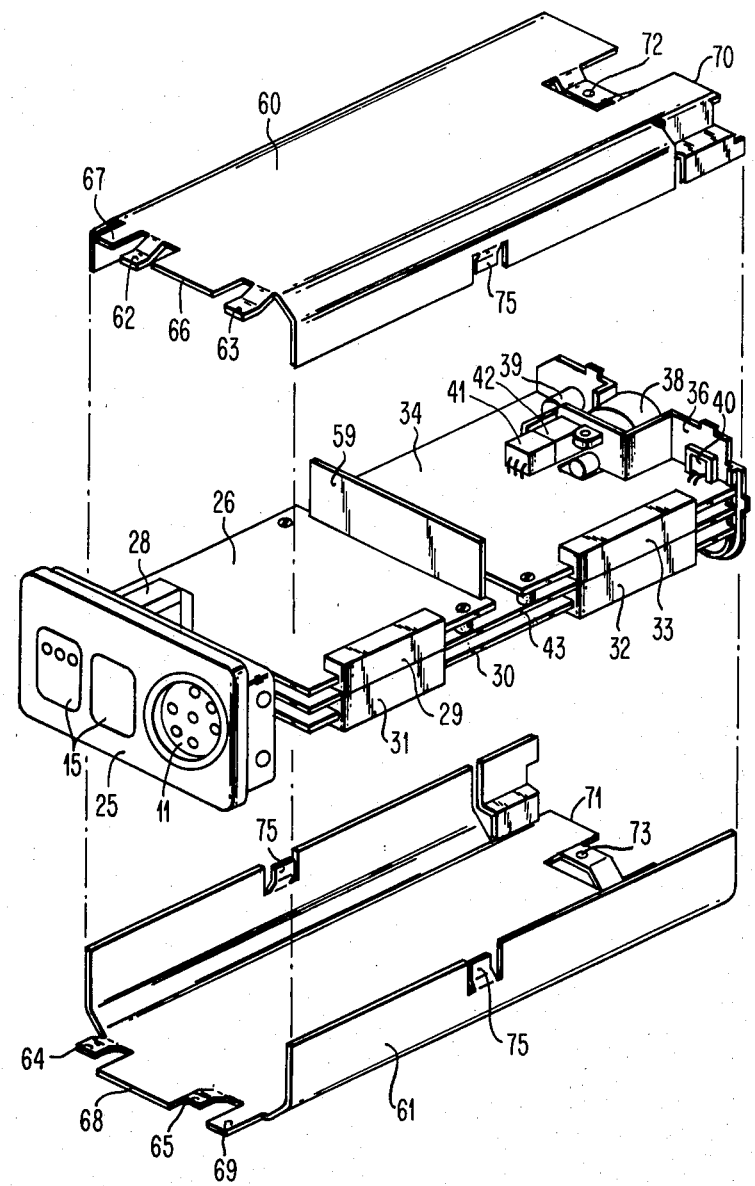
FIG. 6 is a perspective view of a plug-in module containing a layered assembly of printed circuit boards mounted on a front and a back wall, together with shielding sheets.

In FIG. 6 is shown the overall construction of the laminate packet. Here, two outer shielding sheets 60 and 61, e.g. of aluminum or sheet steel, are associated with the central mounting packet in the assembly of the components of FIG. 5. Both shielding sheets 60 and 61 are provided on the front edge with claws 62, 63, and 64, 65, respectively. As the sheet 60 and 61 bears at the flat edges 66, 67 or 68, 69, respectively, on the inner shoulder of the front wall 25, the claws 62 to 65 engage in recesses below the shoulder. There results at the shoulder a kind of clamping connection for retention of the front edge of the two sheets 60 and 61. The rear edges 70 and 71 of the sheets rest on the edges of the back wall 36. They are screwed via holes 72 and 73 to a screw support 74 provided on the back wall 36. The center parts of the shielding sheets 60, 61 elastically engage the lateral edges of the circuit board packet by means of claws 75.

After installation of the shielding sheets 60 and 61, the entire laminate or layered packet can be inserted into the highly insulated case 20 (see FIG. 3) from its front opening. Thus, there results a plug-in module as shown e.g. in FIG. 2. Possible variations of such a plug-in module are shown as modules 4 to 7 in FIG. 1.

While the forms of the plug-in module herein described constitute preferred embodiments of the invention, it is to be understood that the invention is not limited to these precise forms of assembly, and that a variety of changes may be made therein without departing from the scope of the invention.

What is claimed is:

1. A cabinet having
   (1) wall means defining a plurality of recesses designed for sliding insulated plug-in modules therein; and
   (2) a plurality of insulated plug-in modules, each of said plug-in modules being inserted into one of said recesses, respectively, and comprising in combination:
   (a) a case of an insulating material;
   (b) a front wall carrying front connection means, said front connection means being determined for receiving input signals which are specific to a certain application;
   (c) a back wall carrying rear coupling means;
   (d) a first and second plurality of structural elements and components for power and signal transmission and for signal processing, said first and second plurality of elements and components being connected to form respective first and second internal electrical circuits, whereby said first circuits are specific to said application, and whereby said second circuits are identical for various applications and identical for said plurality of plug-in modules;
   (e) a first printed circuit board connected between said front wall and said back wall, said board supporting said first plurality of structural elements and said first plurality of components forming said first circuits which are specific to said application;
   (f) a second printed circuit board mounted on said back wall and arranged parallel to said first printed board, said second board supporting said second plurality of structural elements and said second plurality of components forming said second circuits which are identical for various applications, said second board being inserted along with said first board and said back wall in said case such that said front wall forms the front wall of said case, said case and said front wall thereby forming the housing of said plug-in module.

2. The cabinet according to claim 1, wherein a third printed circuit board is mounted on said front wall and arranged parallel to said first printed circuit board, said third board supporting a third plurality of structural elements and components, said third plurality of components being connected to form third internal electrical circuits which are specific to said input signals of said certain application.

3. The cabinet according to claim 1, wherein a shield is arranged between said first and second printed circuit board and parallel therewith.

4. The cabinet according to claim 3, wherein said shield is an electrically conductive foil.

5. The cabinet according to claim 2, wherein a shielding wall is arranged between said second plurality of components and elements of said second board and said third plurality of components and elements on said third board, said shielding wall being substantially perpendicular to said second and third boards.

6. The cabinet according to claim 5, wherein said shielding wall is mounted on an edge of said third board.

7. The cabinet according to claim 2, wherein the third circuits on said third board are electrically connected to said second circuits on said second board via said first circuits on said first printed circuit board.

* * * * *